United States Patent [19]
Rogers et al.

[11] Patent Number: 5,310,400
[45] Date of Patent: May 10, 1994

[54] THERAPEUTIC BANDAGE

[76] Inventors: Tim S. Rogers, P.O. Box 7863, Santa Rose, Calif. 95407; Frank C. Hammond, 4501 Snell Ave. #2010, San Jose, Calif. 95136

[21] Appl. No.: 979,899
[22] Filed: Nov. 23, 1992
[51] Int. Cl.5 .................. A61F 5/00; A61F 13/00; A61F 5/37
[52] U.S. Cl. .................................. 602/5; 602/13; 602/60; 602/63; 128/882; 128/DIG. 20
[58] Field of Search .............. 602/1, 5, 13, 20, 62, 602/21, 63, 23; 128/882, 878, 879, DIG. 20

[56] References Cited

U.S. PATENT DOCUMENTS

| | | | |
|---|---|---|---|
| 3,351,055 | 11/1967 | Gottfried | 602/13 |
| 3,717,145 | 2/1973 | Berndt | 602/14 |
| 4,146,021 | 3/1979 | Brasseau | 602/62 |
| 4,266,298 | 5/1981 | Graziano | 602/13 |
| 4,378,009 | 3/1983 | Rowley | 602/13 |
| 5,062,414 | 11/1991 | Grim | 128/DIG. 20 |
| 5,085,214 | 2/1992 | Barrett | 128/DIG. 20 |
| 5,139,475 | 8/1992 | Robicsek | 128/DIG. 20 |

Primary Examiner—Michael A. Brown
Attorney, Agent, or Firm—Larry D. Johnson

[57] ABSTRACT

A therapeutic bandage provides a removable bandage article that can be readily wrapped and fastened around an injured joint. The bandage includes an internal air bladder that can be selectively inflated to provide compression to the injury, and an internal coolant bladder that can be selectively chilled to provide cooling therapy to the injury.

5 Claims, 4 Drawing Sheets

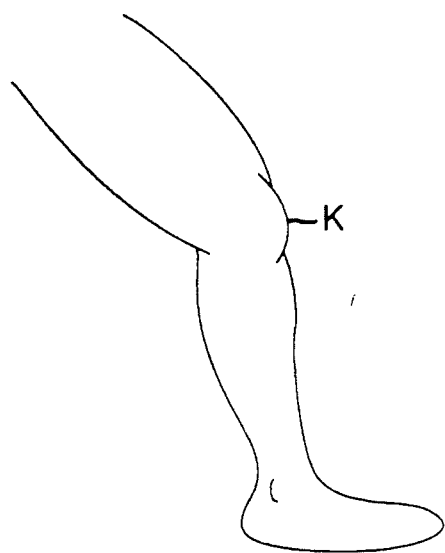
FIG._1A
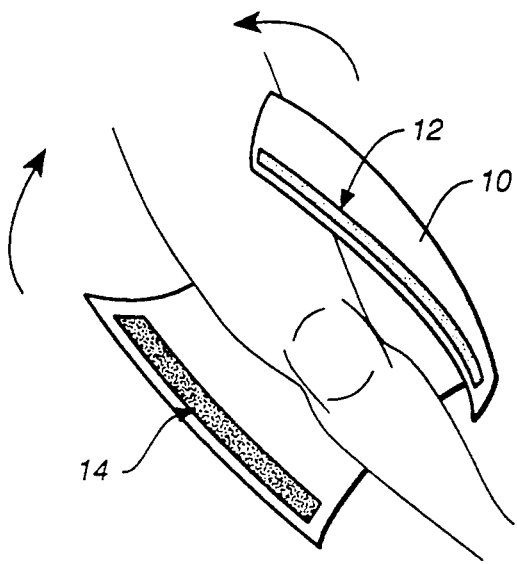
FIG._1B
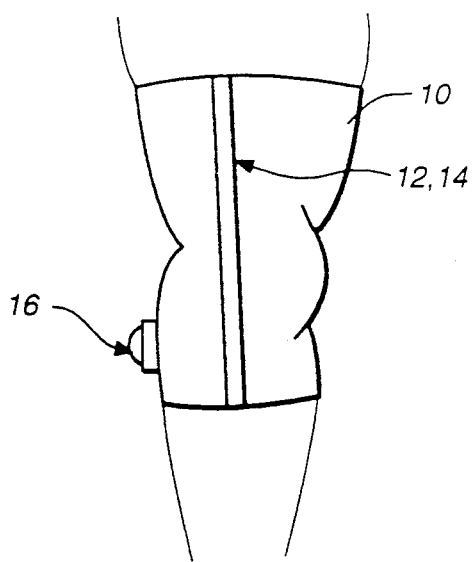
FIG._1C
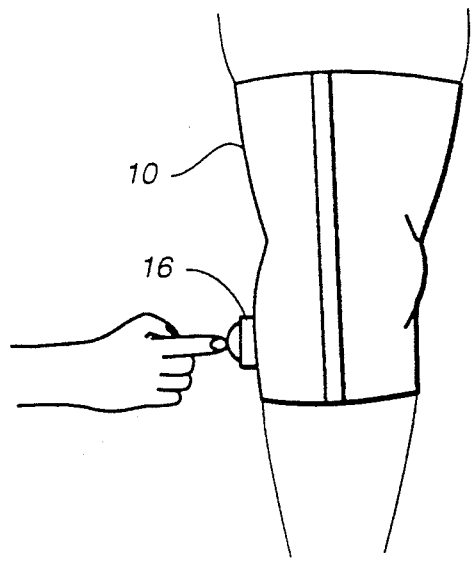
FIG._1D

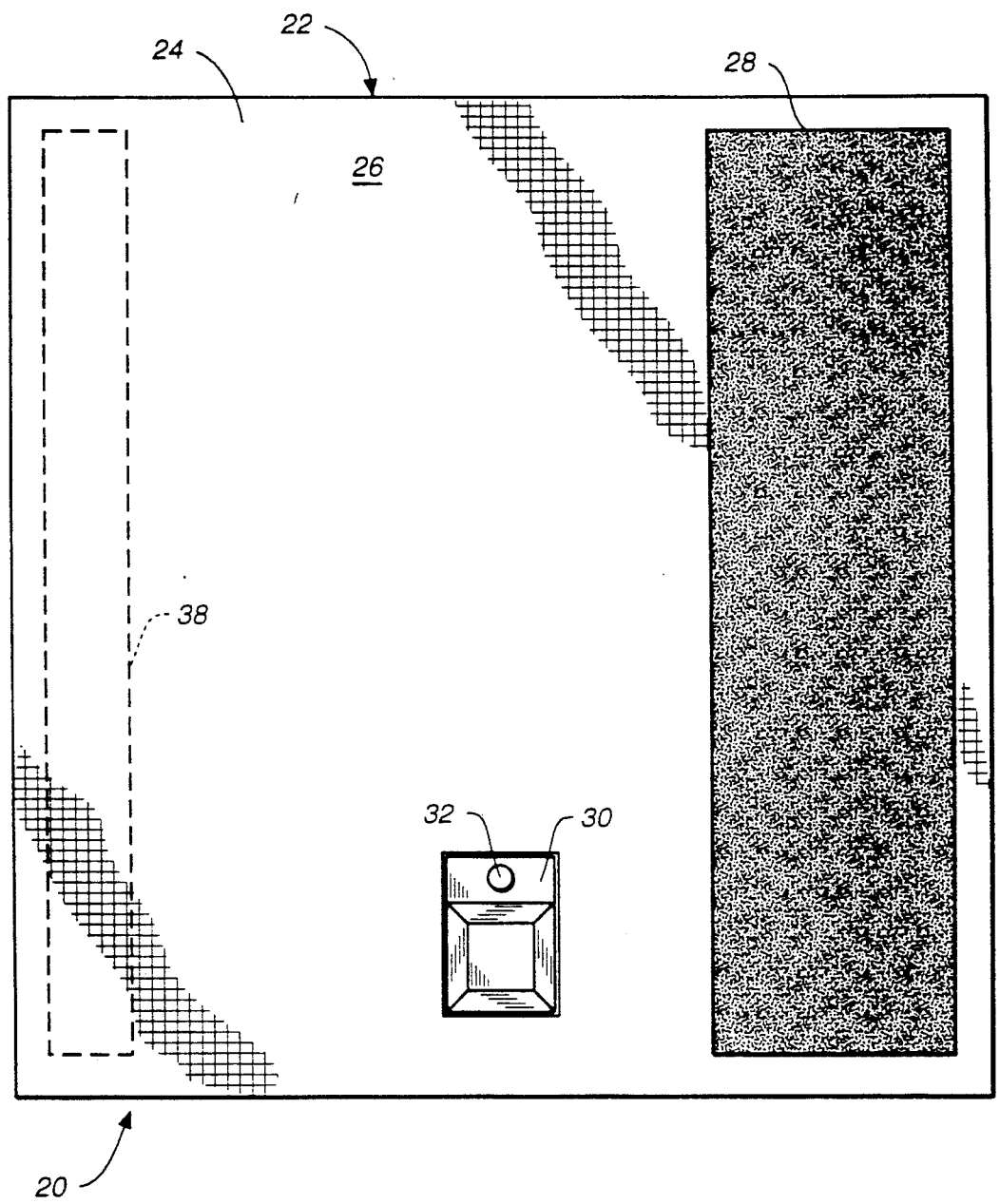
FIG._2

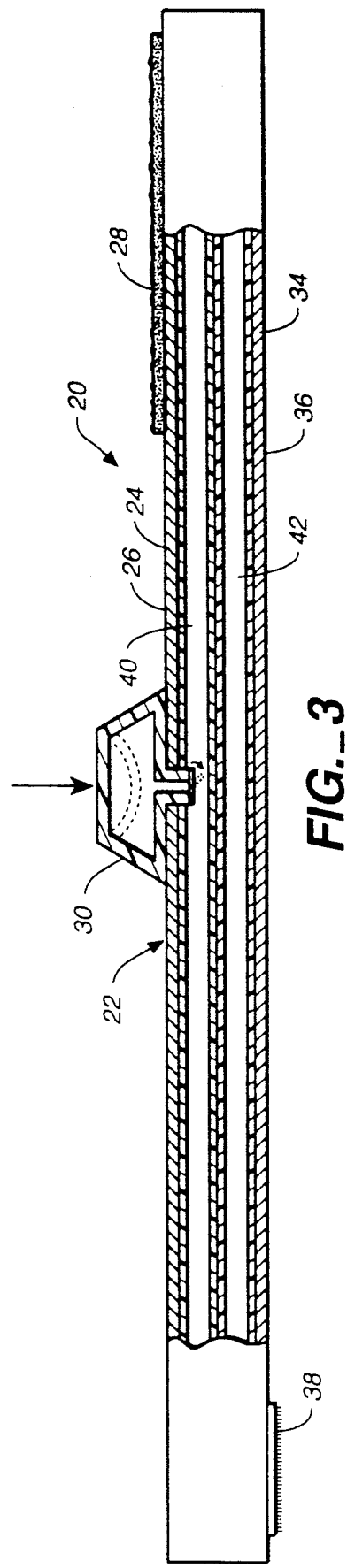
FIG._3

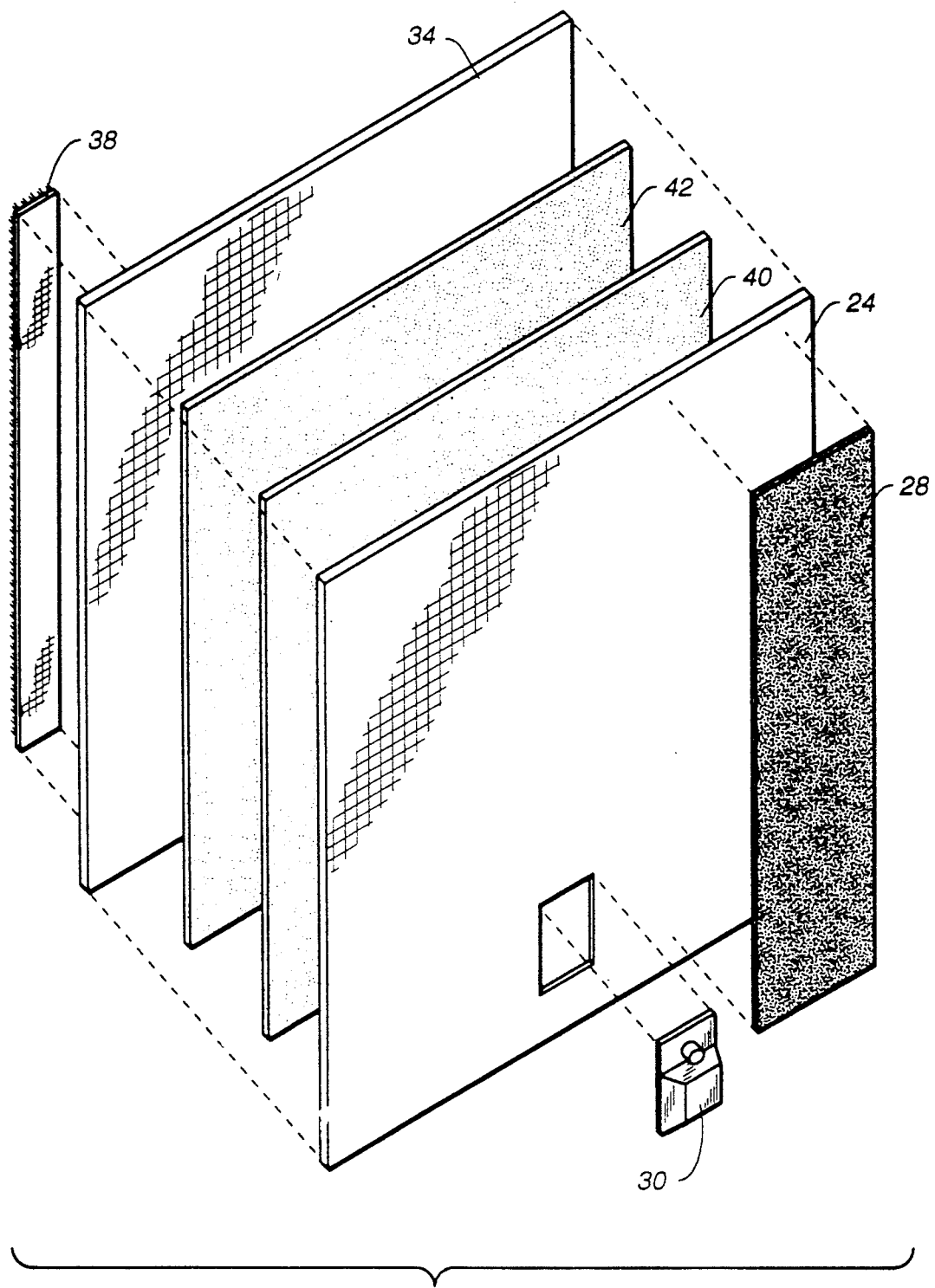
FIG._4

THERAPEUTIC BANDAGE

BACKGROUND OF THE INVENTION

1. Field of the Invention

This invention relates generally to first aid methods and associated medical rehabilitative materials, and more specifically to an improved therapeutic bandage device for efficient treatment of minor injury or discomfort to a user's joints.

2. Description of the Prior Art

Bandages such as those used to support and treat joint injuries are well known. Typically, such bandages consist of a length of elastic material that is wrapped around the joint and secured in place with pins or clamps, thereby temporarily supporting or otherwise immobilizing the joint. However, such known bandages are difficult to adjust in their degree of compression to the injury, and may be awkward to properly apply. In addition, such bandages do not readily enable cooling or chilling of the injured area, which can be important in therapeutic treatment.

SUMMARY OF THE INVENTION

The therapeutic bandage of this invention provides a removable and reusable bandage article that can be readily wrapped and fastened around an injured joint. The inventive bandage includes an internal air bladder that can be selectively inflated so that the bandage exerts provide compression to the injury, and may further include an internal coolant bladder that can be selectively chilled so that the bandage provides cooling therapy to the injury.

The therapeutic bandage of this invention is intended to serve as a non-disposable, repetitive-use device for people who sustain muscle strains or sprains while exercising, or in the treatment of chronic recurring muscle soreness, tendinitis or general inflammation and pain. The inventive device is not intended to serve as a first-aid remedy for compound fractures or any open bleeding wounds. While the inventive device is envisioned to be primarily used on knee-joints, it is foreseen to be equally applicable to other body joints including elbows, shoulders, ankles, wrists, etc.

The inventive bandage body is made of a semi-elastic yet rigid material such as neoprene that is preferably attached to the knee or other joint using complementary strips of sewn-on hook-and-loop type fastener material. The bandage body is attached using the mating fastener strips in a wrap-around fashion about the joint.

Inside the neoprene bandage body is an internal air bladder that is selectively filled with ambient atmospheric air by means of an external manual air pump located on the outer surface of the bandage body. Once the bandage is fastened in place, the user simply inflates the bandage by repeatedly depressing the manual air pump button until the desired degree of compression is attained. The pump includes a one-way valve such that with each depression of the button, the air bladder is further inflated with air, and with each release of the button, the air bladder is sealed. The user may thus regulate the degree of compression exerted by the bandage upon the joint, without manually removing and re-attaching the bandage. To release the air out of the bladder, the user simply twists open the bleed valve, thereby allowing the air to escape. In addition to the compression function of the invention, a coolant-filled reservoir or bladder may be positioned within the bandage body and adjacent to the air bladder. The reservoir may be singular, or may be divided into smaller reservoirs, preferably lining the inner circumference of the bandage. The coolant material itself may be composed of a variety of substances, but is preferably non-toxic. The coolant material should preferably have a low freezing point temperature so as to remain fluid when in use. It is envisioned that prior to applying the bandage, the user would store the inventive bandage in a refrigerator or freezer for a specific period of time (determined by the coolant material, type of injury, and the like).

Thus, the therapeutic bandage of this invention provides a combination of compression and cooling functions for an injured or sprained joint. The inventive device may be made in a range of sizes to fit different joints and different body sizes.

BRIEF DESCRIPTION OF THE DRAWINGS

FIGS. 1a–1d are a series of pictorial views illustrating a therapeutic bandage of this invention being applied to an injured knee;

FIG. 1a is a view of a user's injured knee;

FIG. 1b is a view of a therapeutic bandage of this invention being wrapped around the injured knee such that a complementary set of fastening strips are brought into juxtaposition for releasable fastening;

FIG. 1c is a view of the therapeutic bandage of this invention as applied to the injured knee with the fastening strips sealed together, illustrating a manual air pump actuator exposed for use; and FIG. 1d is a view of the manual air pump actuator being depressed by the user to inflate an internal air bladder (not visible in this view and exert compression to the injured knee;

FIG. 2 is a front elevation view of a therapeutic bandage of this invention in its flattened configuration, illustrating a bandage body; an outside layer with an exposed surface carrying a strip of first fastening material, a manual air pump actuator, and a pressure release valve; with an inside layer on the reverse side with an exposed surface carrying a strip of second fastener material (illustrated in phantom);

FIG. 3 is a bottom end elevation view in partial cross-section of the therapeutic bandage of this invention, illustrating the bandage body, the outside layer exposed surface carrying the strip of first fastening material, the manual air pump actuator, and the pressure release valve; the inside layer exposed surface carrying the strip of second fastening material; an internal air bladder; and an internal coolant bladder; and FIG. 4 is an exploded perspective view of the therapeutic bandage of this invention, illustrating the spatial relationship of the outside layer, internal air bladder, internal coolant bladder, and inside layer.

DETAILED DESCRIPTION OF A PREFERRED EMBODIMENT

FIGS. 1a–1d are a series of pictorial views illustrating a therapeutic bandage of this invention being applied to an injured knee. FIG. 1a is a view of a user's this invention being wrapped around the injured knee such that a complementary set of fastening strips 12, 14 (such as VELCRO brand hook-and-loop fastening material) are brought into juxtaposition for releasable fastening. The fastening strips may alternatively comprise complementary snaps, buttons, zippers, or any other appropriate fastening system. FIG. 1c is a view of the bandage 10 as applied to the injured knee with the fastening strips sealed together, and illustrating a manual air pump actuator 16 exposed for use. FIG. 1d is a view of the manual air pump actuator 16 being depressed by the user to inflate an internal air bladder (not visible in this view) and exert compression to the injured knee.

FIG. 2 is a front elevation view of a therapeutic bandage 20 of this invention in its flattened configuration. This view illustrates a bandage body 22; an outside layer 24 with an exposed surface 26 carrying a strip of first fastening material 28, a manual air pump and actuator 30, and a pressure release valve 32; with an inside layer on the reverse side with an exposed surface carrying a strip of second fastener material (illustrated in phantom).

The therapeutic bandage can of course be made in any size and thickness. For example, a neoprene bandage body with overall dimensions of approximately 12.5 inches by 12.5 inches and a thickness of approximately 0.38 inches, has been determined to be suitable for some applications.

FIG. 3 is a bottom end elevation view in partial cross-section of the therapeutic bandage 20 of this invention, illustrating the bandage body 22, the outside layer 24 exposed surface 26 carrying the strip of first fastening material 28, the manual air pump actuator 30, and the pressure release valve (not visible in this view). This view further illustrates the inside layer 34 exposed surface 36 carrying the strip of second fastening material 38; an internal air bladder 40; and an internal coolant reservoir or bladder 42.

The internal air bladder 40 is of course in fluid communication with the externally-mounted air pump actuator 30 and pressure relief valve 32, but it is otherwise sealed within the bandage body 22. The internal coolant reservoir or bladder 42 is similarly sealed within the bandage body, or could itself form the inside surface 36. The coolant bladder is preferably located proximate the inside surface and below the internal air bladder. This arrangement enables the air bladder to act as an insulator for the coolant material, thereby extending its cooling time and efficiency in use.

FIG. 4 is an exploded perspective view of the therapeutic bandage of this invention, illustrating the spatial relationship of the outside layer 24, the internal air bladder 40, the internal coolant bladder 42, and the inside layer 34. The manual air pump actuator 30 is in fluid communication with the internal air bladder 40, as described supra. The air bladder 40 and the coolant bladder 42 are preferably sealed within outside and inside layers 24, 34, as by sealing around their perimeter edges.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A therapeutic bandage for treatment of minor injury or discomfort to a user's joint, said therapeutic bandage comprising:
   a bandage body having an outside layer and an inside layer;
   fastening means for releasably securing said outside layer to said inside layer when said bandage body is wrapped around a joint;
   a selectively pressurized internal air bladder between said outside layer and said inside layer;
   an air pump carried on said bandage body, said air pump operated by a manually-depressed button and in fluid communication with said internal air bladder; and
   a selectively cooled internal coolant bladder between said outside layer and said inside layer, said internal coolant bladder is positioned between said internal air bladder and said inside layer.

2. The therapeutic bandage of claim 1 further including a pressure relief valve carried on said bandage body, said pressure relief valve in fluid communication with said internal air bladder.

3. The therapeutic bandage of claim 1 wherein said fastening means comprises complementary strips of hook-and-loop fastener material.

4. The therapeutic bandage of claim 1 wherein said bandage body is composed of neoprene.

5. The therapeutic bandage of claim 1 wherein said air pump is carried on said outside layer.

* * * * *